(12) United States Patent
Cuthbertson et al.

(10) Patent No.: US 7,897,142 B2
(45) Date of Patent: Mar. 1, 2011

(54) PEPTIDE BASED-COMPOUNDS

(75) Inventors: Alan Cuthbertson, Oslo (NO); Robert James Nairne, Amersham (GB)

(73) Assignee: GE Healthcare AS, Oslo (NO)

( * ) Notice: Subject to any disclaimer, the term of this patent is extended or adjusted under 35 U.S.C. 154(b) by 1069 days.

(21) Appl. No.: 11/570,156

(22) PCT Filed: Jun. 15, 2005

(86) PCT No.: PCT/NO2005/000210
§ 371 (c)(1),
(2), (4) Date: Dec. 7, 2006

(87) PCT Pub. No.: WO2005/123768
PCT Pub. Date: Dec. 29, 2005

(65) Prior Publication Data
US 2008/0095715 A1    Apr. 24, 2008

(30) Foreign Application Priority Data
Jun. 16, 2004  (NO) .................................. 20042523

(51) Int. Cl.
*A61B 10/00* (2006.01)
*A61B 5/00* (2006.01)

(52) U.S. Cl. ...... 424/9.6; 424/1.11; 424/1.65; 424/1.69; 424/9.1

(58) Field of Classification Search ................. 424/1.11, 424/1.65, 1.69, 9.1, 9.3, 9.4, 9.5, 9.6, 9.7, 424/9.8, 9.2; 514/2, 9, 10, 11; 530/300, 326, 327, 328, 329, 330, 331, 333, 338
See application file for complete search history.

(56) References Cited

U.S. PATENT DOCUMENTS

| | | | |
|---|---|---|---|
| 7,351,790 B2 * | 4/2008 | Cuthbertson et al. | 530/317 |
| 7,521,419 B2 * | 4/2009 | Cuthbertson et al. | 514/10 |
| 7,608,243 B2 * | 10/2009 | Cuthbertson et al. | 424/1.69 |

FOREIGN PATENT DOCUMENTS

| | | |
|---|---|---|
| WO | 01/77145 | 10/2001 |
| WO | 03/006491 | 1/2003 |
| WO | 2005/003166 | 1/2005 |

OTHER PUBLICATIONS

PCT/NO2005/000210 International Search Report and Written Opinion dated Oct. 12, 2005.
Chen, X, et.al., "In vivo near-infrared fluorescence imaging of integrin .alpha.v.beta.3 in braintumor xenografts" Cancer Research vol. 64, No. 21, Nov. 1, 2004 pp. 8009-8014.
Achilefu, S, et.al. "Synergistic effects of light-emitting probes and peptides for targeting and monitoring integrin expression" Proceedings of the National Academy of science, USA, vol. 102, No. 22, May 31, 2005 pp. 7976-7981.

* cited by examiner

*Primary Examiner* — D L Jones

(57) ABSTRACT

The invention relates to new peptide-based compounds and their use in diagnostic optical imaging techniques. More specifically the invention relates to the use of such peptide-based compounds as targeting vectors that bind to receptors associated with angiogenesis. The compounds are labelled with at least one cyanine dye reporter and may be used as contrast agents in optical imaging in diagnosis of angiogenesis-related diseases.

17 Claims, No Drawings

SEQUENCE LISTING

<160> NUMBER OF SEQ ID NOS: 8

<210> SEQ ID NO 1
<211> LENGTH: 8
<212> TYPE: PRT
<213> ORGANISM: Artificial sequence
<220> FEATURE:
<223> OTHER INFORMATION: Synthetic peptide

<400> SEQUENCE: 1

Lys Cys Arg Gly Asp Cys Phe Cys
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Asp Cys Arg Gly Asp Cys Phe Cys
1               5

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Lys Asp Cys Arg Gly Asp Cys Phe Cys Gly
1               5                   10

<210> SEQ ID NO 4
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(8)
<223> OTHER INFORMATION: Thioether bridge between amino acid residue 1
      and 8
<220> FEATURE:
<221> NAME/KEY: DISULFID
<222> LOCATION: (2)..(6)
<223> OTHER INFORMATION: Disulphide bridge between amino acid residue 2
      and 6

<400> SEQUENCE: 4

Lys Cys Arg Gly Asp Cys Phe Cys
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(8)
<223> OTHER INFORMATION: Thioether bridge between amino acid residue 1
      and 8
<220> FEATURE:
<221> NAME/KEY: DISULFID

```
<222> LOCATION: (2)..(6)
<223> OTHER INFORMATION: Disulphide bridge between amino acid residue 2
      and 6

<400> SEQUENCE: 5

Asp Cys Arg Gly Asp Cys Phe Cys
1               5

<210> SEQ ID NO 6
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(3)
<223> OTHER INFORMATION: Thioether bridge between amino acid residue 1
      and 3
<220> FEATURE:
<221> NAME/KEY: DISULFID
<222> LOCATION: (7)..(9)
<223> OTHER INFORMATION: Disulphide bridge between amino acid residue 7
      and 9

<400> SEQUENCE: 6

Lys Asp Cys Arg Gly Asp Cys Phe Cys Gly
1               5                   10

<210> SEQ ID NO 7
<211> LENGTH: 5
<212> TYPE: PRT
<213> ORGANISM: Artificial sequence
<220> FEATURE:
<223> OTHER INFORMATION: Synthetic peptide

<400> SEQUENCE: 7

Asp Phe Lys Arg Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(5)

<400> SEQUENCE: 8

Asp Phe Lys Arg Gly
1               5
```

PEPTIDE BASED-COMPOUNDS

This application is a filing under 35 U.S.C. 371 of international application number PCT/NO2005/000210, filed Jun. 15, 2005, which claims priority to application number 20042523 filed Jun. 16, 2004, in Norway the entire disclosure of which is hereby incorporated by reference.

This invention relates to new peptide-based compounds and to their use in diagnostic optical imaging techniques or for the treatment of disease. More specifically the invention relates to the use of such peptide-based compounds as targeting vectors that bind to receptors associated with angiogenesis. The compounds may be used as contrast agents in diagnosis of angiogenesis-related diseases or for treatment of such.

Generally, new blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Inhibition of angiogenesis is also considered to be a promising strategy for antitumour therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Further examples of undesired conditions that are associated with neovascularization or angiogenesis, the development or proliferation of new blood vessels are shown below. Reference is also made in this regard to WO 98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous malformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

Angiogenesis involves receptors that are unique to endothelial cells and surrounding tissues. These markers include growth factor receptors such as VEGF and the Integrin family of receptors. Immunohistochemical studies have demonstrated that a variety of integrins, perhaps most importantly the $\alpha_v$ class, are expressed on the apical surface of blood vessels [Conforti, G., et al. (1992) Blood 80: 37-446] and are available for targeting by circulating ligands [Pasqualini, R., et al. (1997) Nature Biotechnology 15: 542-546]. The $\alpha5\beta1$ is also an important integrin in promoting the assembly of fibronectin matrix and initiating cell attachment to fibronectin. It also plays a crucial role in cell migration.

The integrin $\alpha v\beta3$ is one of the receptors that is known to be associated with angiogenesis. Stimulated endothelial cells appear to rely on this receptor for survival during a critical period of the angiogeneic process, as antagonists of the $\alpha v\beta3$ integrin receptor/ligand interaction induce apoptosis and inhibit blood vessel growth.

Integrins are heterodimeric molecules in which the $\alpha$- and $\beta$-subunits penetrate the cell-membrane lipid bilayer. The $\alpha$-subunit has four $Ca^{2+}$ binding domains on its extracellular chain, and the $\beta$-subunit has a number of extracellular cysteine-rich domains.

Many ligands (eg. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. Perhaps the most widely studied effect of RGD peptides and mimetics thereof relate to their use as anti-thrombotic agents where they target the platelet integrin GpIIbIIIa.

Inhibition of angiogenesis in tissues by administration of either an $\alpha v\beta3$ or $\alpha v\beta5$ antagonist has been described in for example WO 97/06791 and WO 95/25543 using either antibodies or RGD containing peptides. EP 578083 describes a series of mono-cyclic RGD containing peptides. Cyclic RGD peptides containing multiple bridges have also been described in WO 98/54347 and WO 95/14714.

Further examples of RGD comprising peptide-based compounds are found in WO01/77145, WO02/26776 and WO 03/006491. WO01/177145 discloses bicyclic RGD-type peptides conjugated with a reporter moiety. WO05/003466 further discloses RGD-type peptides conjugated with fluorescein for use in optical imaging.

There is a clinical need to develop more specific non-invasive imaging techniques for angiogenesis-related diseases and for therapy of such diseases. Such imaging techniques will have a central role in the evaluation of novel anti-angiogenic therapies. Being able to assess the actual level of angiogenesis will be of clinical benefit in diagnosing angiogenesis-related diseases at an early stage. Optical imaging may be used to assess the level of angiogenesis, and the invention provides new compounds useful as optical imaging contrast agents for this purpose.

In view of the needs of the art the invention provides peptide-based compounds labelled with cyanine dyes for use as contrast agents in optical imaging or for therapeutic treatment. The efficient targeting and imaging of integrin receptors associated with angiogenesis in vivo demands a selective, high affinity RGD-type vector that is chemically robust and stable. Furthermore, the route of excretion is an important factor when designing imaging agents in order to reduce problems with background noise. These stringent conditions are met by the cyanine dye labelled peptide compounds described in the present invention.

Viewed from one aspect the invention provides new peptide-based compounds as defined in the claims. These compounds have affinity for integrin receptors, e.g. affinity for the integrin αvβ3, and are labelled with a cyanine dye reporter.

The compounds, or physiologically acceptable salts thereof, comprise a peptidic vector and at least one cyanine dye, wherein the peptidic vector comprises the amino acid sequence $X_3$-G-D and wherein the peptidic vector and the at least one cyanine dye are coupled, preferably by a covalent bond. $X_3$ represents arginine, N-methylarginine or an arginine mimetic, G represents glycine and D represents aspartic acid. The peptidic vector has affinity for integrin receptors, such as the αvβ3 receptors.

The cyanine dye (CyDye™) is in the following represented by the letter Z. Cyanine dyes are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. General description of cyanine dyes and synthesis thereof are described in U.S. Pat. Nos. 6,048,982 and 5,268,486 which are hereby incorporated by reference. The cyanine dyes are particularly useful due to the wide range of spectral properties and structural variations available. A range of cyanine dyes are well known and tested, they have low toxicity, and are commercially available (GE Healthcare, formerly Amersham Biosciences). The cyanine dyes are a single family of highly intense dyes with good aqueous solubility. They are pH insensitive between pH 3-10, exhibit low non-specific binding, and are more photostable than fluorescein.

A preferred embodiment of this invention allows for cyanine dyes to be conjugated to the peptidic vectors resulting in reduced blood pool retention. This embodiment of the invention provides for a compound comprising cyanine dyes with two, one or no sulphonic acid moieties. Dyes with a reduced number of sulphonic acid moieties when conjugated to peptides such as the RGD peptide, possess lower blood plasma binding and reduced non-specific binding to background tissue. Sulphonic acid groups do impart some hydrophilicity to the dyes, a necessary feature for in vivo imaging. Cyanine dyes have traditionally been used in vitro where the polysulphonation of the dyes was important to make the dyes very water soluble. It has surprisingly been discovered that by removing sulphonic acid groups from the dye, more optimal biodistribution of compounds was experienced.

In this embodiment of the invention we preferably use cyanine dyes each comprising 2, 1 or no sulphonic acid moieties to reduce the blood-plasma binding and non-specific binding of the peptide-based compound. The compounds were surprisingly found to be sufficiently hydrophilic to be soluble in water.

The cyanine dye is preferably selected from the groups consisting of carbacyanines, oxacyanines, thiacyanines and azacyanines shown below by general formulas.

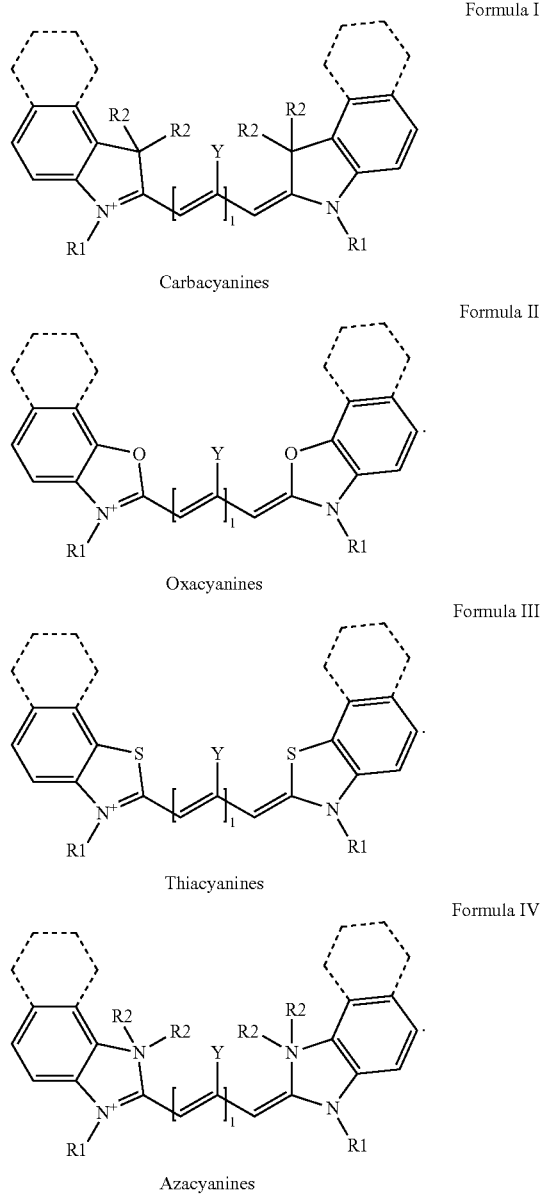

Formula I
Carbacyanines

Formula II
Oxacyanines

Formula III
Thiacyanines

Formula IV
Azacyanines

In these structures the R1-groups are the same or different and are substituted or unsubstituted alkyl groups, preferably C1 to C6 alkyls, and may comprise an ether or an —N—CO—N— group The alkyl groups are optionally substituted with carboxy, sulphonic acid, amine, ammonium or ester groups. The R1-groups may form bridges with any of the carbon-atoms of the polyene chains, e.g. by a —N—CO—N— group or an ether-group. The R2-groups are also the same or different and are substituted or unsubstituted alkyl groups. The alkyl groups are optionally substituted with carboxy or sulphonic acid groups, but preferably the R2-groups are lower alkyl groups, such as C1 to C6 alkyls, and most preferably methyl groups. Optional aromatic groups are indicated by dotted lines, to cover both structures comprising condensed benzo rings and condensed naphtho rings. The rings are substituted or unsubstituted. The rings may be substituted with sulphonic acid groups, carboxylic groups, hydroxyl groups, alkyl(sulphoalkyl)amino groups, bis(sulphoalkyl)amino groups, sulphoalkoxy groups, sulphoalkylsulphonyl group, alkyl or substituted alkyl or sulphoalkylamino groups. The alkyl-groups are preferably lower alkyls with e.g. 1 to 6 carbon atoms. Y is selected from hydrogen, a halide group, amine group or an sulphonyl, and is preferably hydrogen. The polyene chain of the cyanine dye may also contain one or more cyclic chemical group that forms bridges between two or more of the carbon atoms of the polyene chain, e.g. by including a —CO— group between two of the carbon atoms of the chain, as in the squaraine dyes, or by including an alkyl bridge. These bridges might serve to increase the chemical or photostability of the dye.

In the formulas I to IV I is a positive integer 1, 2, 3 or 4 giving trimethinecyanines, having a carbon-bridge of three carbon atoms, pentamethine, heptamethine or nonamethine cyanine dyes. Preferably, the cyanine dye is a pentamethine or a heptamethine dye with carbon-bridges of 5 and 7 carbon atoms, respectively.

Referring to formula I-IV preferred dyes have altogether 2, 1 or no sulphonic acid moieties attached to the indole rings or benzeindole rings.

Preferred dyes are selected from the group of carbacyanines. And even more preferred are the carbacyanine dyes of the indole type. Preferred dyes of this type are illustrated by formula V:

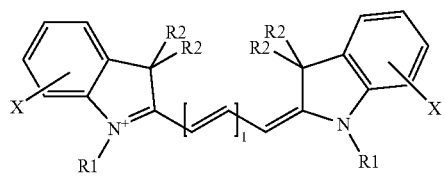

(V)

wherein X is a sulphonic acid moiety or is absent, the R1 groups are the same or different and are substituted or unsubstituted lower alkyl groups, e.g. C1 to C6 alkyl groups which are optionally substituted. The alkyl groups are substituted e.g. with carboxy, sulphonic acid, amine, ammonium or ester groups, such as heterocyclic ester groups (e.g. NHS-ester). The R2 groups are lower alkyl groups, such as C1 to C6 alkyls, preferably methyl groups, optionally substituted with e.g. carboxy or sulphonic acid groups. I is 1, 2 or 3.

R1, R2 and X are potential linking sites for the linking of the dye to the peptidic vector, the R1 and X group being preferred. In a preferred aspect one R1 group is linked to the peptidic vector while the other R1 group is a optionally substituted lower alkyl group.

Most preferred dyes are the Cy5 mono NHS-ester bis $SO_3$ and the Cy7 mono NHS-ester bis $SO_3$ shown below:

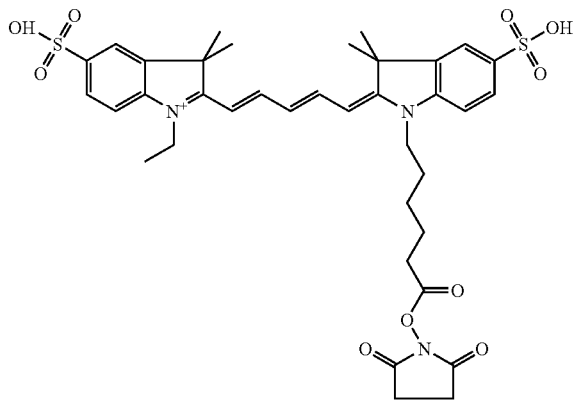

Cy5 mono NHS-ester bis $SO_3$

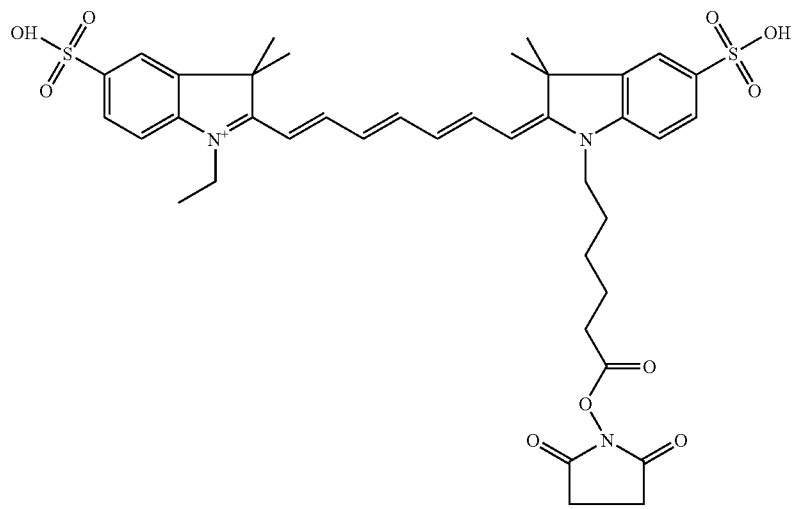

Cy7 mono NHS-ester bis SO$_3$

Suitable cyanine dyes for use in the compounds of the invention have an emission spectrum in the visible or near infra red range, preferably in the range of 500-900 nm, and more preferably in the range of 650-850 nm.

The compounds of the invention comprise the amino acid sequence X$_3$-G-D having affinity for the integrin receptors. The compound preferably comprises further amino acids, and optional other moieties, wherein the X$_3$-G-D sequence is the binding seat of the peptidic vector which functions as a vector binding to an integrin type receptor.

The compound of the invention can be constrained for example by formation of one or more cyclising bridges in the peptidic vector part. A monocyclic peptide compound can be obtained by formation of a disulphide bond or a thioether bond between amino acids. A peptide-based compound including one cyclising bridge is more specific towards αvβ3, and is more preferred, than a linear peptide. The compounds of the invention preferably comprise two cyclising bridges between different amino acids of the compounds or between amino acids and other moieties. The term "cyclising bridges" refers to any combination of amino acids with functional groups which allows for the introduction of a bridge, or between amino acids and —(CH$_2$)$_n$— or —(CH$_2$)$_n$—C$_6$H$_4$— groups. n represents a positive integer from 1 to 10. Some preferred examples are disulphides, disulphide mimetics such as the —(CH$_2$)$_4$— carba bridge, thioacetal, thioether bridges (cystathione or lanthionine) and bridges containing esters and ethers. Preferably, one bridge forms a disulphide bond and a second bridge comprises a thioether (sulphide) bond.

In a further embodiment the compound of the invention are identified by formula (VI a)

A-Z       (VI a)

wherein A is identified by the formula (VI b)

R$_a$-C(=O)-X$_1$-X$_2$-X$_3$-G-D-X$_4$-X$_5$-X$_6$-X$_7$       (VI b)

and Z represents at least one cyanine dye, linked to one or more of X$_1$, X$_6$ or X$_7$ of A, optionally via a spacer group, the compound comprising two cyclising bridges, wherein, X$_3$, G and D are as previously defined;

R$_a$ represents —(CH$_2$)$_n$— or —(CH$_2$)$_n$—C$_6$H$_4$— group, which forms part of a bridge binding to either of X$_2$, X$_4$ or X$_6$, wherein n represents a positive integer from 1 to 10;

X$_1$ represents a bond or 1, 2, 3, 4 or 5 amino acid residues, wherein at least one amino acid residue is optionally functionalised with a spacer moiety, and preferably said amino acid residue possesses a functional side-chain such as an acid or amine group, and is preferably selected from aspartic or glutamic acid, homolysine, or a diaminoalcylic acid such as lysine, or diaminopropionic acid; and X$_2$ and X$_4$ represent independently amino acids residues capable of forming a cyclising bridge, such as cysteine or homocysteine residues forming disulphide or thioether bonds, or other amino acid residues capable of forming a cyclising bridge such as aspartic acid and lysine, preferably X$_2$ and X$_4$ represent residues of cysteine or homocysteine, and preferably X$_2$ and X$_4$ form cyclising bridges between each other or with R$_a$ or X$_6$; and X$_5$ represents a hydrophobic amino acid or derivatives thereof, and preferably represents a tyrosine, a phenylalanine, a 3-iodo-tyrosine or a naphthylalanine residue, and more preferably a phenylalanine or a 3-iodo-tyrosine residue; and X$_6$ represents an amino acid residue capable of forming a cyclising bridge, preferably a thiol-containing amino-acid residue, preferably a cysteine or a homocysteine residue, and preferably X$_6$ forms a cyclising bridge with R$_a$, X$_2$ or X$_4$; and X$_7$ represents a spacer or biomodifier moiety or is absent, and is preferably comprising a monodisperse polyethylene glycol (PEG) building block comprising 1 to 10 units of said building block, said biomodifier having the function of modifying the pharmacokinetics and blood clearance rates of said agents. In addition X$_7$ may also represent 1 to 10 amino acid residues preferably comprising glycine, lysine, aspartic acid or serine. X$_7$ may also represent a spacer or biomodifier comprising both amino acid residues and a PEG-like structure, preferably a bis aminoethyl ethylene glycol glycine combination. In a preferred embodiment X$_7$ represents a unit comprised of the monodisperse PEG-like structure, 17-amino-5-oxo-6-aza-3,9,12,15-tetraoxaheptadecanoic acid of formula (X),

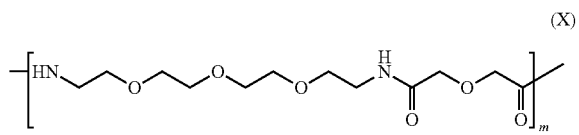

(X)

wherein m equals an integer from 1 to 10 and where the C-terminal is an amide or acid moiety. It is found that the biomodifier, X$_7$, modifies the pharmacokinetics and blood clearance rates of the compounds. The biomodifier effects lower uptake of the compounds in tissue i.e. muscle, liver etc. thus giving a better diagnostic image due to less background interference. The secretion is mainly through the kidneys and this represents a further advantage of the biomodifier.

The peptide-based compound comprises a peptidic vector defined by the amino sequence formed by X$_1$, X$_2$, X$_3$, G, D, X$_4$, X$_5$ and X$_6$ of Formula VI b and this peptide constitute a targeting vector having affinity for integrin receptors associated with angiogenesis.

Depending of the placement of the cyclising bridges the compounds will comprise "discrete", "nested" or "interlocking" configurations. Preferably the two bridges in each compounds are:

Between R$_a$ and X$_6$, and between X$_2$ and X$_4$ (forming a nested configuration);

Between R$_a$ and X$_2$, and X$_4$ and X$_6$ (discrete configuration);

Between R$_a$ and X$_4$, and X$_2$ and X$_6$ (forming an interlocking configuration).

In a preferred embodiment one bridge forms a thioether bond and the second bridge forms a disulphide bond.

In a further embodiment the compounds of the invention are identified by either of the formulas below:

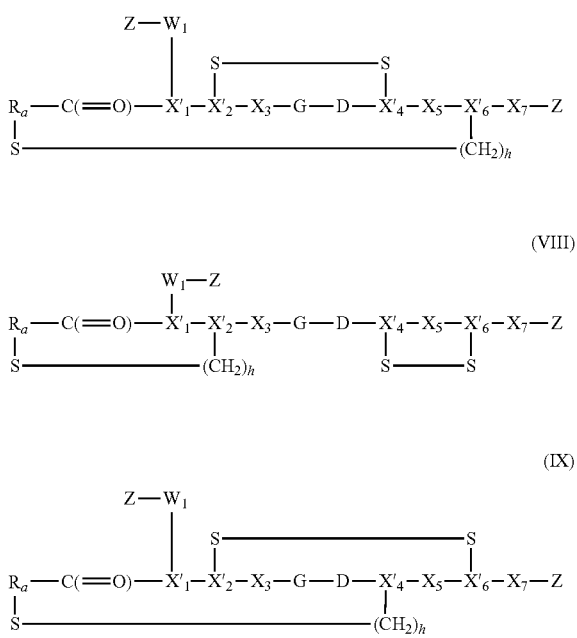

wherein $R_a$, $X_3$, G, D, $X_5$, and $X_7$ are as defined for formula VI b; and wherein $X'_1$ comprises an amino acid residue with a functional side-chain such as an acid or amine group, the amino acid preferably being selected from aspartic or glutamic acid, homolysine or a diaminoalcylic acid such as lysine or diaminopropionic acid, more preferably aspartic acid or lysine;

$X'_2$, $X'_4$ and $X'_6$ represent amino acid residues forming a disulphide or a thioether bond, such as cysteines or homocysteines, the disulphide and thioether bonds being shown;

$W_1$ is a spacer moiety or is absent, and is preferentially derived from glutaric and/or succinic acid and/or a polyethylenglycol based unit linking the cyanine dye reporter to the peptide. Other representative spacer ($W_1$) elements include structural-type polysaccharides, storage-type polysaccharides, polyamino acids and methyl and ethyl esters thereof, and polypeptides, oligosaccharides and oligonucleotides, which may or may not contain enzyme cleavage sites. The role of the spacer moiety $W_1$ is to distance the relatively bulky dye from the receptor binding domain of the peptide component;

h is a positive integer 1 or 2;

and wherein at least one of the Z groups is present, Z representing a cyanine dye.

The compounds preferably include only one Z-group.

The cyanine dye, represented by Z is linked to $X'_1$, $W_1$, $X_6$ or $X_7$ of the peptidic vector e.g. by formation of an amide linkage, a sulphonamide linkage or a thioether linkage. An amide linkage is e.g. formed from reaction between an amine and carboxylic group, a sulphonamide linkage is e.g. formed from reaction between an amine and an activated sulphonic acid, and a thioether linkaged is e.g. formed from reaction between a thiol and a halide. $X'_1$ of the peptidic vector, comprising at least one amino acid with a functional side chain, constitutes a preferred attachment point for the cyanine dye. Active esters of the cyanine dyes such as the NHS esters are considered particularly useful when synthesising the compounds forming an amide bond to the peptidic vector.

In a preferred aspect the compounds of formula VII-IX, or the physiologically acceptable salts thereof, have the following characteristics:

$R_a$ preferably represents —$(CH_2)$—.

Further, $X'^1$ represents an amino acid residue with a functional side-chain such as an acid or amine group, the amino acid preferably being selected from aspartic or glutamic acid, homolysine or a diaminoalcylic acid such as lysine or diaminopropionic acid, more preferably aspartic acid or lysine.

$X'_2$, $X'_4$ and $X'_6$ independently preferably represent a cysteine or a homocysteine residue.

$X_3$ preferably represents arginine.

$X_5$ preferably represents tyrosine, phenylalanine, 3-iodotyrosine or naphthylalanine, and more preferably phenylalanine or 3-iodo-tyrosine.

$X_7$ and $W_1$ are as defined for formula VI b. Preferably $X_7$ comprises 1-10 units of a monodisperse PEG building block or is absent, and $W_1$ is preferably absent.

Z represents a cyanine dye or is absent, such that the compound comprises at least one cyanine dye moiety.

In a preferred aspect the compounds are of formula VII (nested) or physiologically acceptable salts thereof, and more preferably they have the characteristics given above.

Any of the amino acid residues as defined in formula VI b may preferably represent a naturally occurring amino acid. In most cases, it is preferred that the amino acids in the peptidic vector are all in the L-form. However, in some embodiments of the invention one, two, three or more of the amino acids in the peptide are preferably in the D-form. The inclusion of such D-form amino acids can have a significant effect on increasing the serum stability of the compound.

Some of the compounds of the invention are high affinity RGD-type vectors. As used herein the term 'high affinity RGD-type vector' refers to compounds that have a Ki of <10 nM and preferably <5 nM, in a competitive binding assay for $\alpha v\beta 3$ integrin and where the Ki value was determined by competition with the known high affinity ligand echistatin. Methods for carrying out such competition assays are well known in the art.

Compounds defined by the present invention are surprisingly stable in vivo and under the conditions employed during labeling with a cyanine dye.

Some examples of compounds of the invention are illustrated below. Compounds A, B and C comprise a pentamethine carbacyanine with respectively one, two or four sulphonic acid groups conjugated to an RGD-containing peptide (Lys-Cys-Arg-Gly-Asp-Cys-Phe-Cys). Compounds A and B comprise a Cy5 dye, while compound C comprises a Cy5.5 dye:

Compound A:
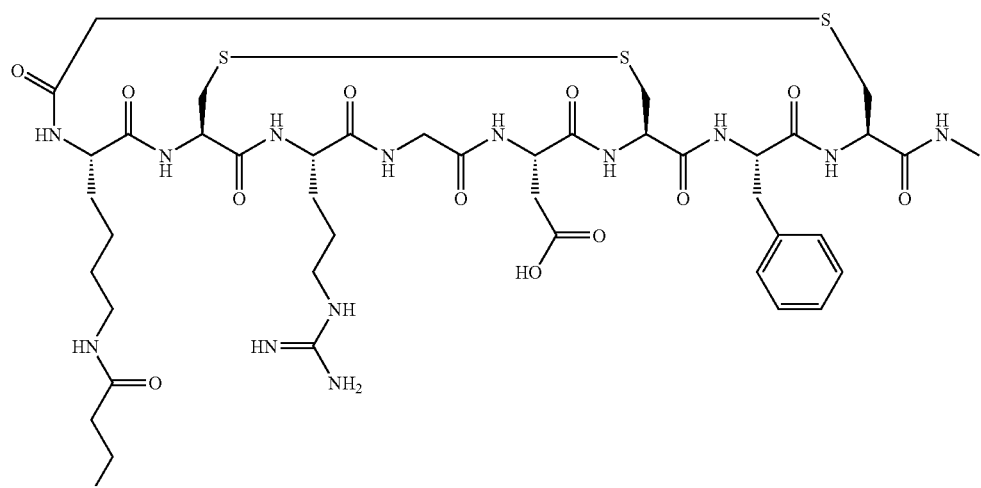
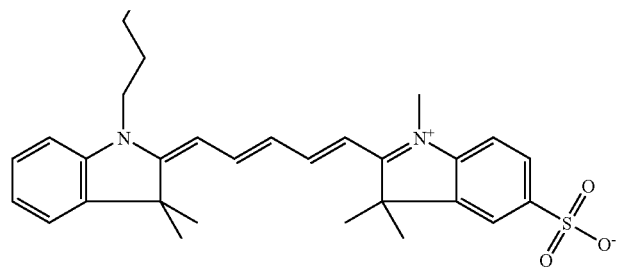
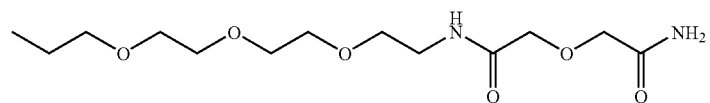
Compound B:
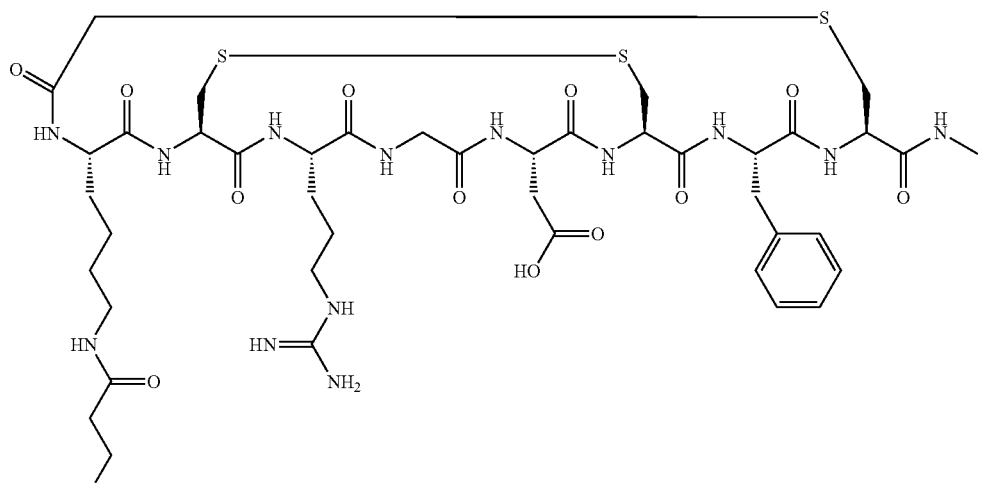

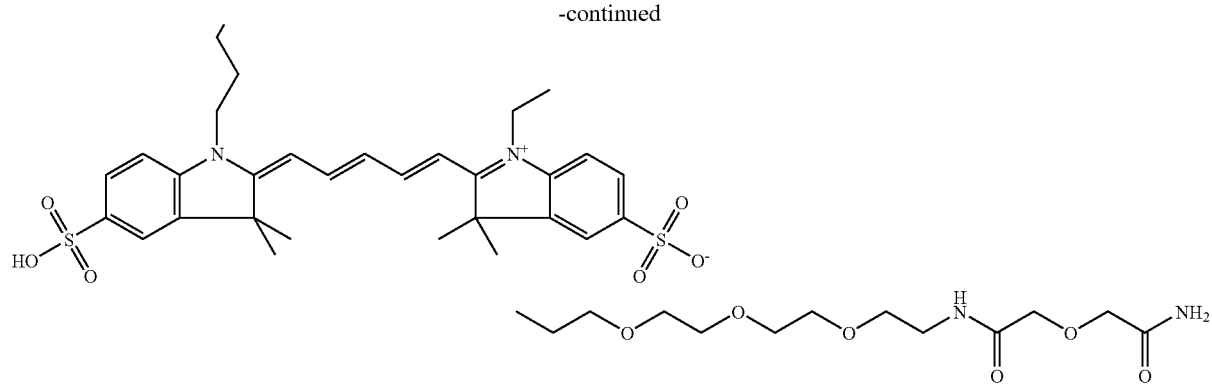
Compound C:
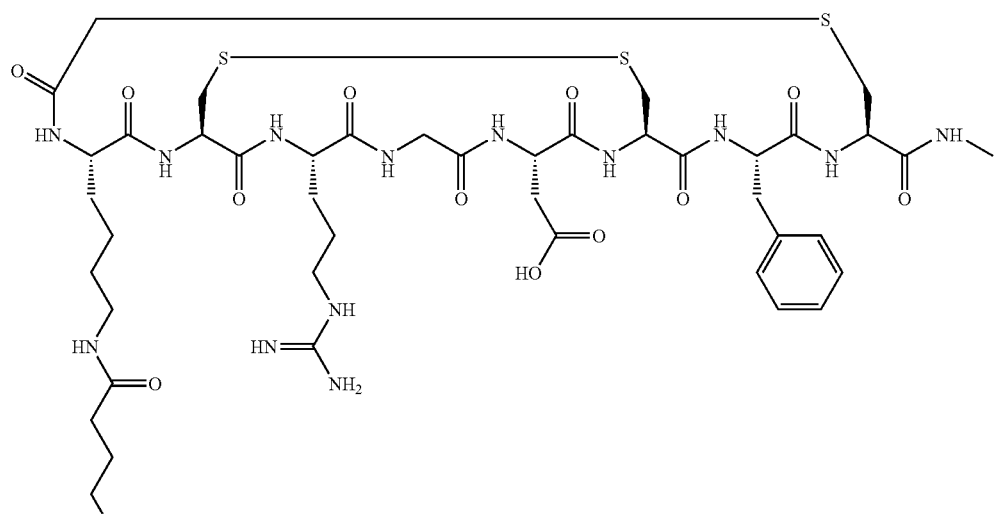
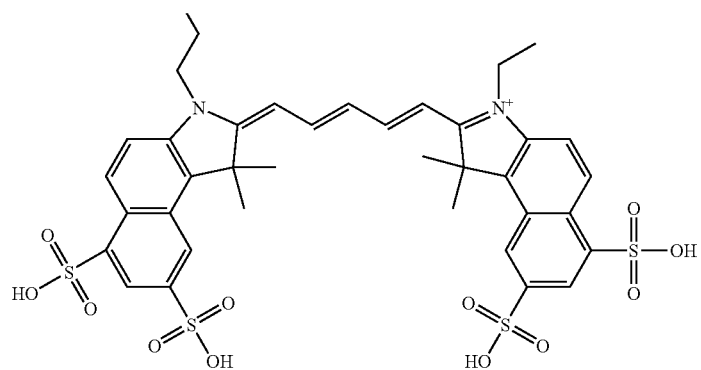
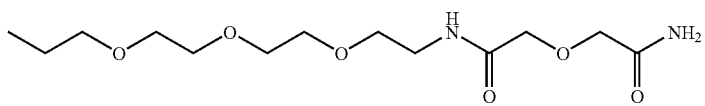

Compound D:
The compound comprises an RGD-type peptide (Lys-Cys-Arg-Gly-Asp-Cys-Phe-Cys) linked to two cyanine dye groups (Cy5).
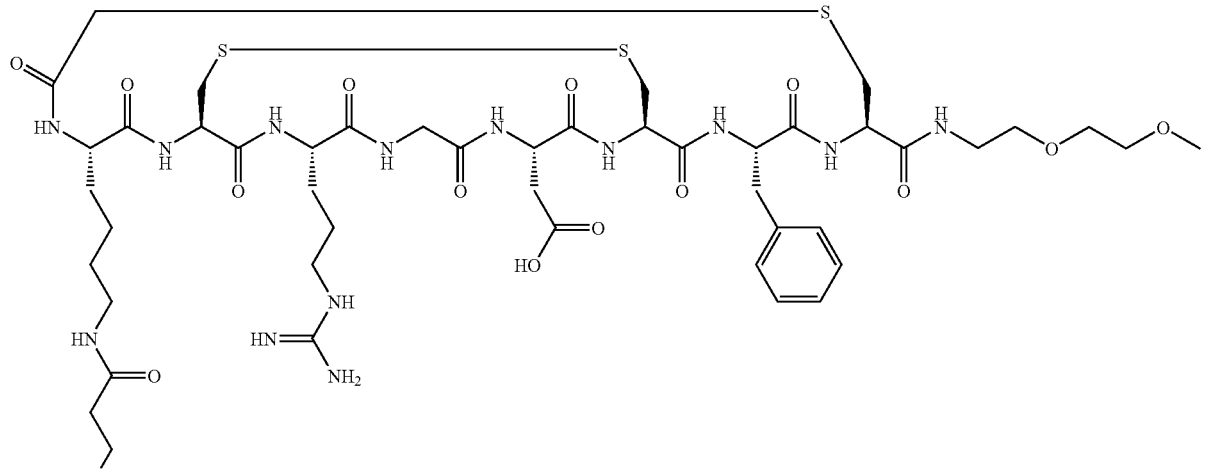
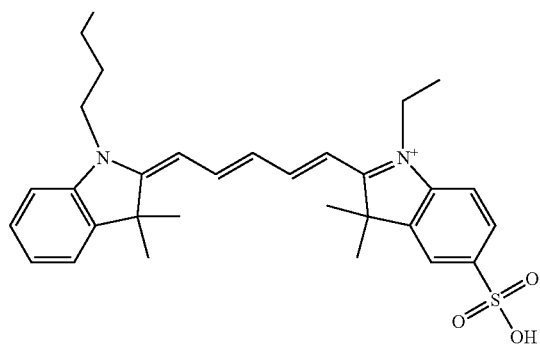
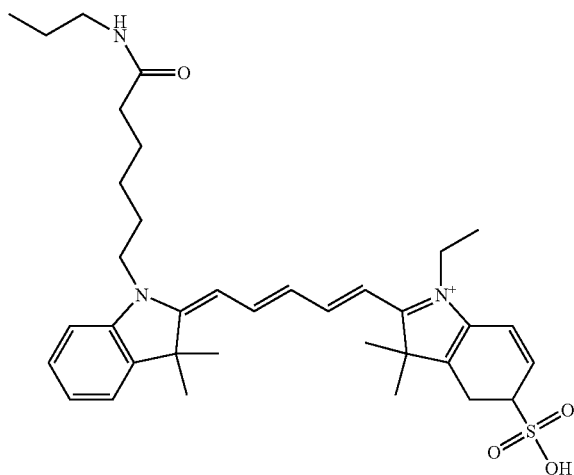

Compound E: The compound comprises the peptide Lys-Cys-Arg-Gly-Asp-Cys-Phe-Cys linked to indocyanine green (ICG).
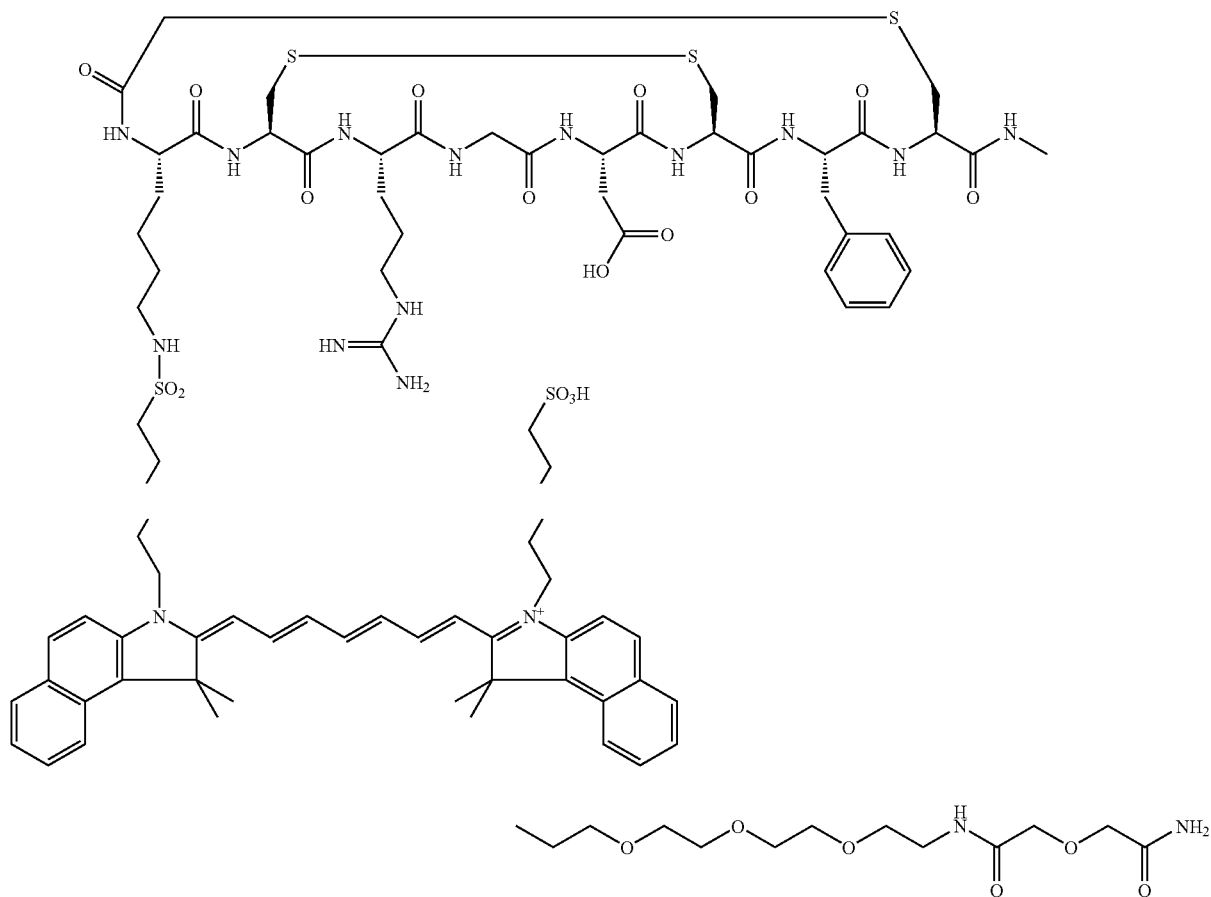
Compound F:
The compound comprises the peptide Lys-Cys-Arg-Gly-Asp-Cys-Phe-Cys linked to Cy3B.
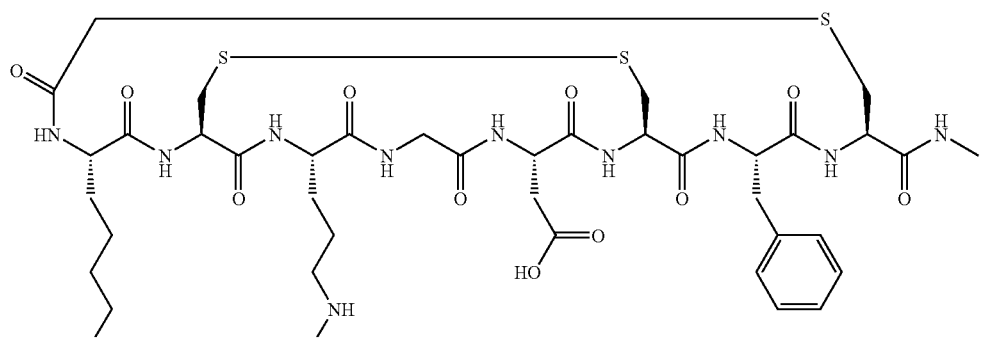

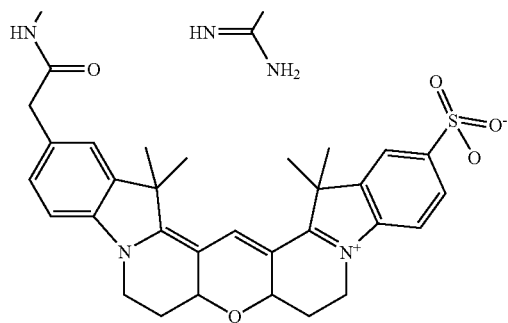
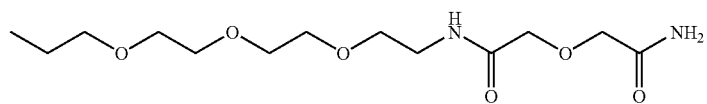
Compound G:
The compound comprises the peptide Lys-Cys-Arg-Gly-Asp-Cys-Phe-Cys linked to a Cy5 wherein R1 is an alkyl substituted with an ammonium group.
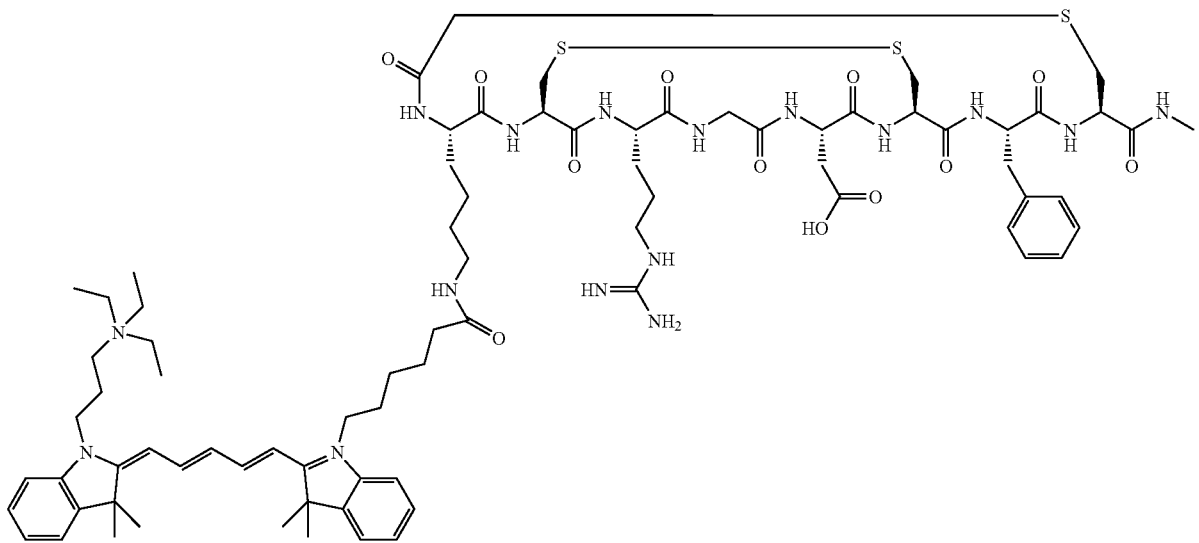
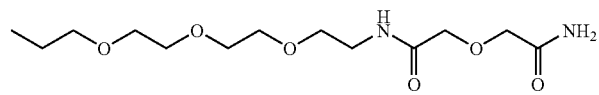

Compound H:

The peptide compound shown below comprising an Asp-Cys-Arg-Gly-Asp-Cys-Phe-Cys peptide can be linked to a cyanine dye by linking the aspartic acid ($X_1$) to an amino-functionalised cyanine dye or by reacting a cyanine dye NHS-ester with the amino-PEG positioned at $X_7$.

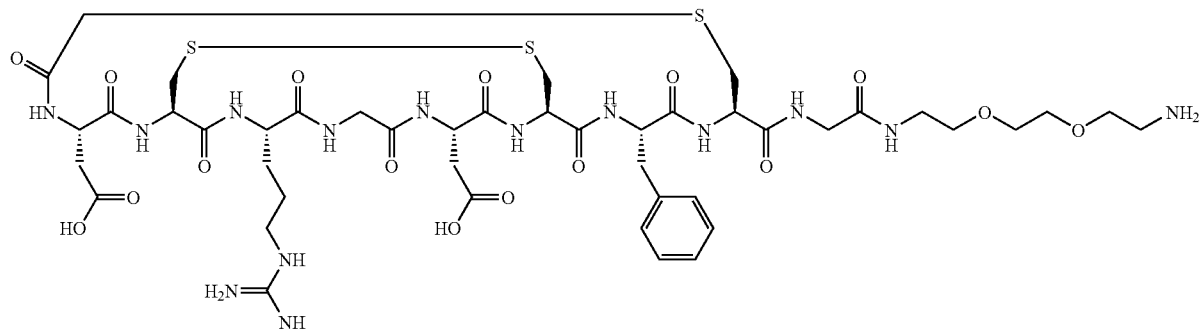

Molecular Weight = 1143.29
Exact Mass = 1142
Molecular Formula = C44H66N14O16S3

Compound I:

The compound comprises the peptide Lys-Asp-Cys-Arg-Gly-Asp-Cys-Phe-Cys-Gly linked to a Cy5.

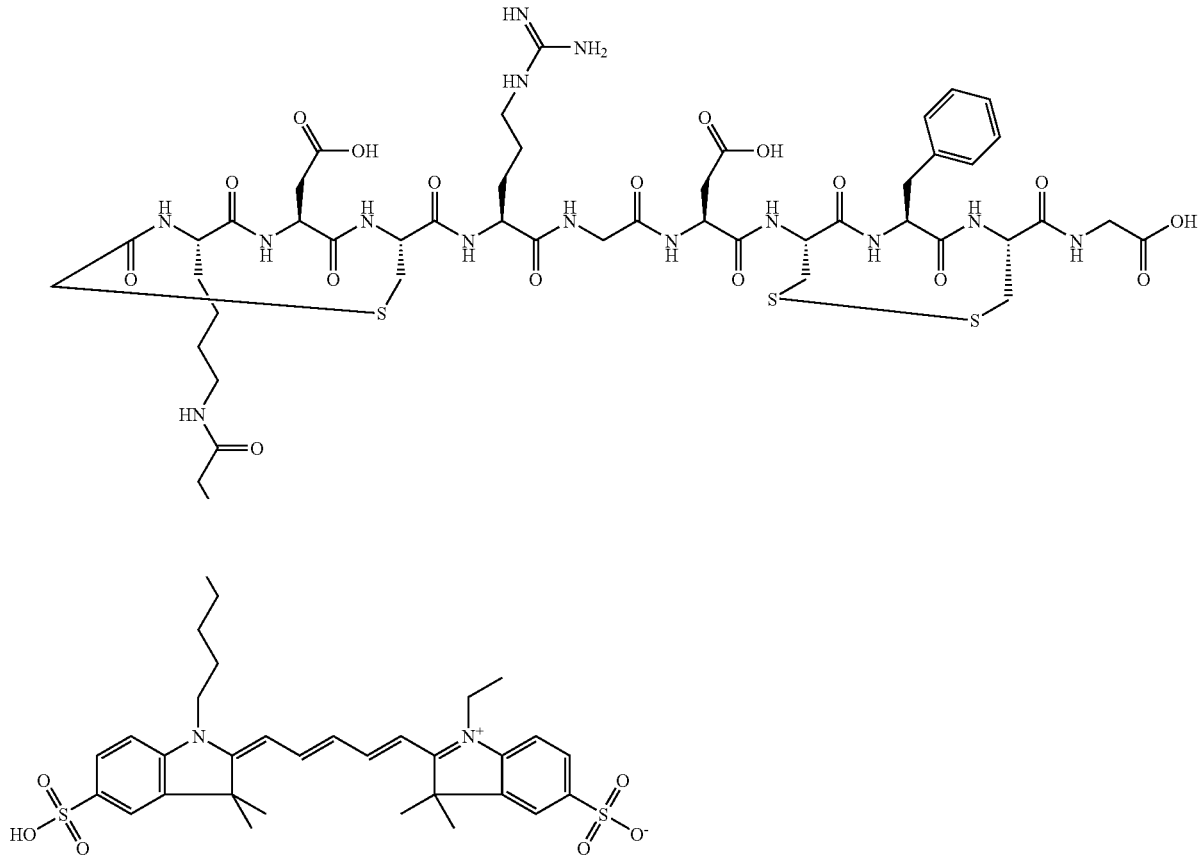

Compound J: c[-Asp-D-Phe-Lys(Cy5.5)-Arg-Gly-]

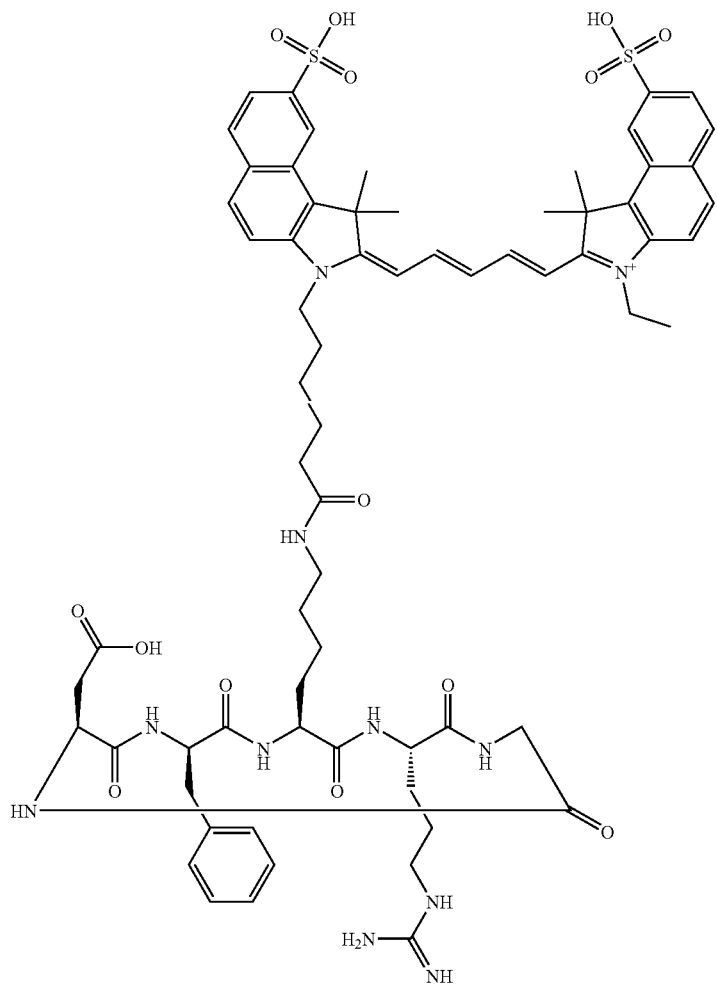

The new compounds of the invention may be used as contrast agents in optical imaging or for treatment of diseases. A preferred embodiment of the invention is compounds as described for use in optical imaging and preferably for diagnosing of angiogenesis-related diseases.

The compounds of this invention are useful as imaging agents in the detection of angiogenesis in both humans and animals. The products may also have utility in pre-clinical animal models and allow monitoring of therapeutic efficacy of new drugs within pharmaceutical research, e.g. in oncology.

The present invention also provides a pharmaceutical composition comprising an effective amount, e.g. an amount effective for enhancing image contrast in in vivo imaging of a compound of the invention or a salt thereof, together with one or more pharmaceutically acceptable adjuvants, excipients or diluents.

The invention further provides a pharmaceutical composition for treatment of a disease comprising an effective amount of the compound, or a salt thereof, together with one or more pharmaceutically acceptable adjuvants, excipients or diluents. The composition may be used in treatment of angiogenesis-related diseases, e.g. by photodynamic therapy.

Viewed from a further aspect the invention provides the use of a compound of the invention for the manufacture of an optical imaging contrast agent for use in a method of diagnosis involving administration of said contrast agent to a human or animal body and generation of an image of at least part of said body.

Use of the compounds in the manufacture of therapeutic compositions (medicament) and in methods of therapeutic or prophylactic treatment, preferably treatment of angiogenesis-related diseases, of the human or animal body are thus considered to represent further aspects of the invention.

Viewed from a still further aspect the invention provides a method of generating an image of a human or animal body by optical imaging involving administering a contrast agent to said body, e.g. into the vascular system and generating an image of at least a part of said body, to which said contrast agent has distributed, wherein as said contrast agent is used a compound as described.

Viewed from a still further aspect the invention provides a method of generating enhanced images of a human or animal body by optical imaging previously administered with a contrast agent composition comprising a compound as defined, which method comprises generating an image of at least part of said body.

Viewed from a further aspect the invention provides a method of monitoring the effect of treatment of a human or animal body with a drug to combat a condition associated with angiogenesis, said method involving administering to said body a compound as described and detecting the uptake of said agent by cell receptors, preferably endothelial cell receptors and in particular αvβ3 receptors, said administration and detection optionally but preferably being effected repeatedly, e.g. before, during and after treatment with said drug. Said detection comprising an optical imaging technique.

The contrast agents of the invention are intended for use in optical imaging. Any method that forms an image for diagnosis of disease, follow up of disease development or for follow up of disease treatment based on interaction with light in the electromagnetic spectrum from ultraviolet to near-infrared radiation falls within the term optical imaging. Optical imaging includes all methods from direct visualization without use of any device and use of devices such as various scopes, catheters and optical imaging equipment, for example computer based hardware for tomographic presentations. The contrast agents will be useful with optical imaging modalities and measurement techniques including, but not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarisation, luminescence, fluorescence lifetime, quantum yield, and quenching. Diagnostic optical imaging methods based on fluorescence identification or measurements are preferred.

The peptitic vectors of the compounds of the present invention can be synthesized using known methods of chemical synthesis and particularly useful is the solid-phase methodology of Merrifield employing an automated peptide synthesizer (J. Am. Chem. Soc., 85: 2149 (1964)). In addition, coupling of a cyanine dye, such as a cyanine dye active ester, can also be carried out automatically employing an automated peptide synthesizer yielding an amide bond between the peptide and the cyanine dye moiety. Other linkages between the cyanine dye and the peptide, such as thioether or sulphone amide linkages may also be obtained automatically, or the reaction of the dye and the peptide may be carried out by ordinary manual chemical synthesis. Synthesis of peptides by solid phase techniques is based upon the sequential addition of protected amino acids linked, optionally through a linker group, to a solid phase support. In one commonly employed method, the α-amino group is suitably protected with acid labile or base labile protecting groups. Following addition and coupling of the first amino acid residue, the α-amino protecting group is removed. The chain is extended by the sequential addition of further protected amino acid derivatives or peptide fragments and/or suitably derivatised and protected cyanine dye derivatives. In this way, a dye-labelled peptide compound according to the invention may be constructed by sequential addition of amino acids or a cyanine dye derivative.

Peptidic vectors containing multiple bridges are synthesised using different cysteine protecting groups so that no ambiguity exists as to the final folded form of the vector. The synthesis disclosed in WO03/006491, describing how the peptides, including thioether and disulphide bridges are formed, may be used. Thioether cyclisation may e.g. be carried out in the following way: The Cys(t-Bu)-protected peptide is dissolved in water/acetonitril (1 mg/ml). The mixture is adjusted to pH 8 using diluted ammonia solution and the mixture is stirred over night. Disulphide bridges may be formed by DMSO/THF oxidation in the following way: The peptide is dissolved in 5 % DMSO/TFA (1 mg/ml) and the mixture is stirred for 30 minutes.

Cyanine dyes are commercially available from GE Healthcare, formerly Amersham Biosciences, e.g. Cy5 NHS ester, 1 mg, PA 15101.

The peptidic vectors and peptide compounds may be purified using high performance liquid chromatography (HPLC) and characterized by mass spectrometry and analytical HPLC before testing in the in vitro screen.

The present invention will now be further illustrated by way of the following non-limiting examples.

EXAMPLES

Abbreviations:
TSTU: O-(N-Succinimidyl)-N,N,N', N'-tetramethyluronium tetrafluoroborate
TFA: Trifluoroactic acid
DMF: N,N-Dimethylformamide
NMM: N-Methylmorpholine Example 1

Synthesis of Cys2-6; c[CH$_2$CO-Lys(Cy5 mono-SO$_3$)-Cys-Arg-Gly-Asp-Cys-Phe-Cys]-(PEG)n-NH$_2$
(n=1)

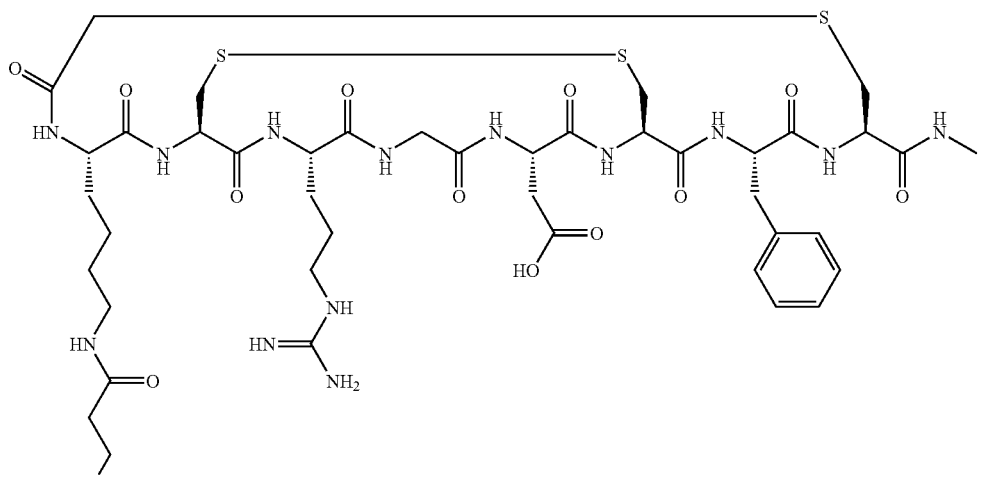

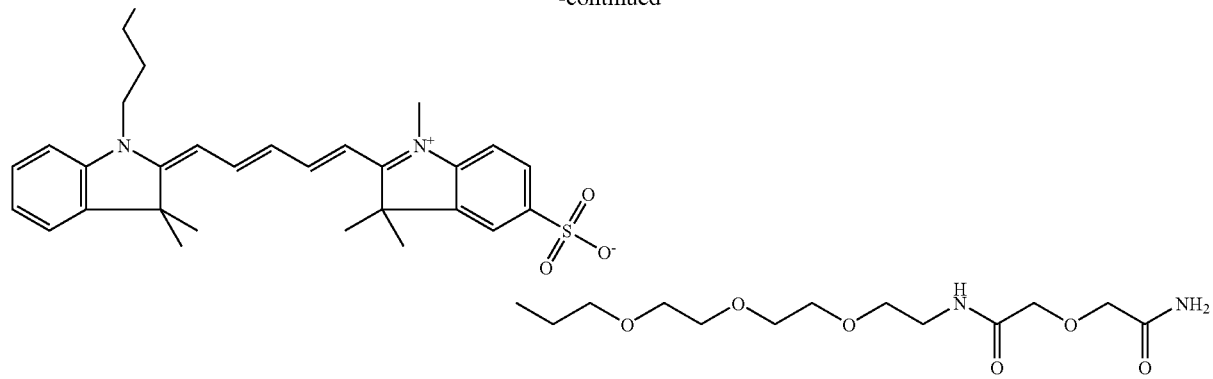

The peptide above was assembled using standard solid phase peptide synthesis methods. The chloroacetylated peptide was cleaved from the solid support and cyclized in solution, first forming the thioether bridge and then the disulphide bridge. The NHS-ester of Cy5 mono acid mono-$SO_3$ (4.5 mg, 0.008 mmol) was formed by treatment with TSTU (2.1 mg, 0.0076 mmol) and NMM (0.009 ml, 0.08 mmol) in DMF (2 ml) for 1 h. The solution was then added to the peptide (20 mg, 0.016 mmol) and the reaction was let proceed over night avoid from light. DMF was evaporated under reduced pressure and the crude product was purified by reverse phase preparative chromatography (Vydac C18 column, 218TP1022; solvents: A=water/0.1% TFA and B=$CH_3CN$/0.1% TFA; gradient 20-40% B over 60 min; flow 10 ml/min; detection at 254 nm), affording 4.9 mg (34%) of pure product (analytical HPLC: Phenomenex Luna C18 column, 00G-4252-E0; solvents: A=water/0.1% TFA and B=$CH_3CN$/0.1% TFA; gradient 25-45% B over 20 min; flow 1.0 ml/min; retention time 15.2 min; detection at 214 and 254 nm). Further characterisation was carried out using mass spectrometry, giving m/z value 902.1 [$MH^{2+}$].

Example 2

Synthesis of Cys2-6; c[$CH_2$CO-Lys(Cy5 bis-$SO_3$)-Cys-Arg-Gly-Asp-Cys-Phe-Cys]-(PEG)n-$NH_2$ (n=1)

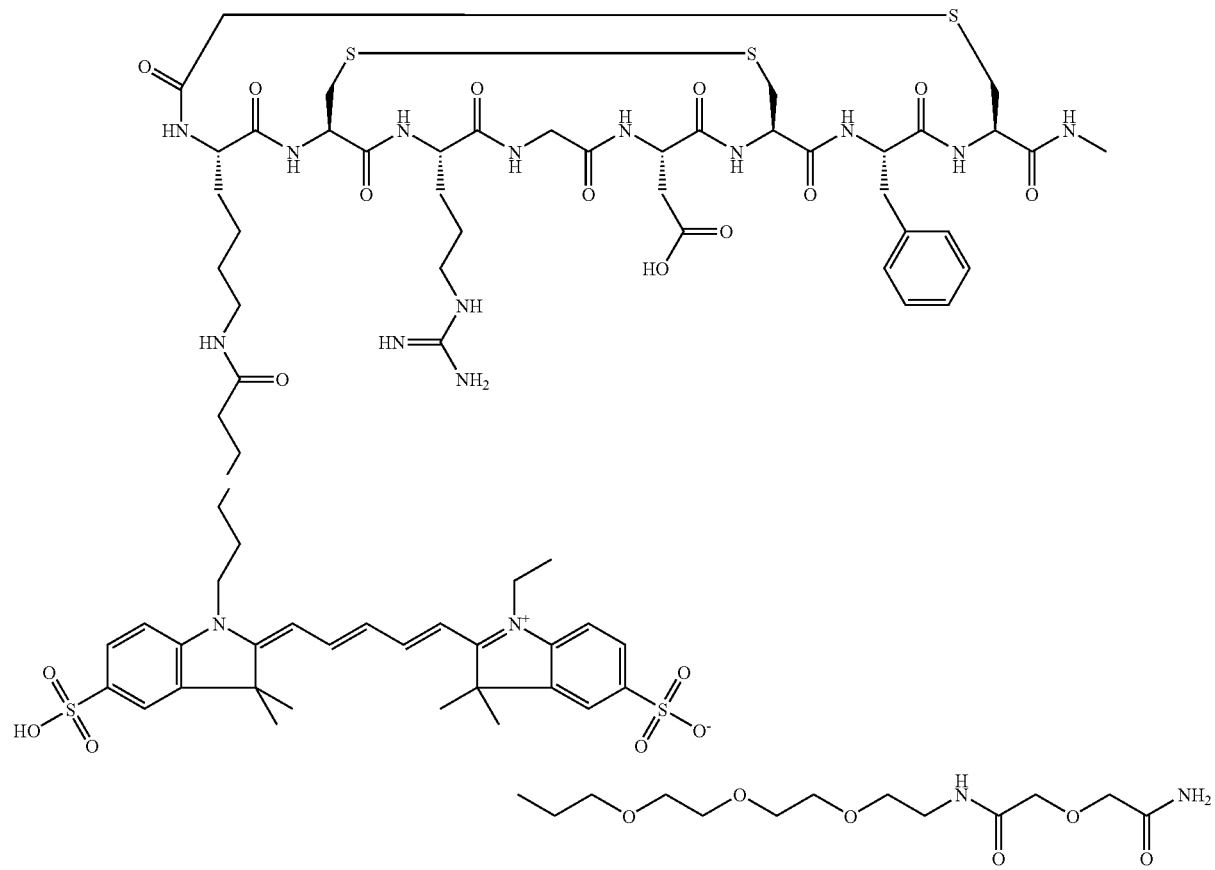

The peptide above was assembled using standard solid phase peptide synthesis methods. The chloroacetylated peptide was cleaved from the solid support and cyclized in solution, first forming the thioether bridge and then the disulphide bridge. The bicyclic peptide (24 mg, 0.02 mmol) was added as a solid to a solution of Cy5 mono NHS-ester bis-SO$_3$ (7.5 mg, 0.01 mmol) in DMF (2 ml), and NMM (0.01 ml, 0.09 mmol) was then added. The reaction was let proceed over night avoid form light. DMF was evaporated under reduced pressure and the crude product was purified by reverse phase preparative chromatography (Vydac C18 column, 218TP1022; solvents: A=water/0.1% TFA and B═CH$_3$CN/0.1% TFA; gradient 10-30% B over 60 min; flow 10 ml/min; detection at 254 nm), affording 6.6 mg (37%) of pure product (analytical HPLC: Phenomenex Luna C18 column, 00G-4252-E0; solvents: A=water/0.1% TFA and B═CH$_3$CN/0.1% TFA; gradient 15-35% B over 20 min; flow 1.0 ml/min; retention time 19.5 min; detection at 214 and 254 nm). Further characterisation was carried out using mass spectrometry, giving m/z value 949.1 [MH$^{2+}$].

Example 3

Synthesis of Cys2-6; c[CH$_2$CO-Lys(Cy7 bis-SO$_3$)-Cys-Arg-Gly-Asp-Cys-Phe-Cys]-(PEG)n-NH$_2$ (n=1)

The conjugate above was assembled using standard solid phase synthesis methods. The chloroacetylated peptide was cleaved from the solid support and cyclized in solution by first forming the thioether bridge and then the disulphide bridge. The NHS-ester of Cy7 mono acid bis-SO$_3$ was formed by treating Cy7 (5.4 mg, 1 eq) with TSTU (2.1 mg, 0.95 eq) and NMM (5 eq) in DMF (2 ml) for 1 h. The solution was then added to the peptide (18.9 mg, 0.015 mmol, 2 eq) in DMF (2 ml) and the reaction was let go in the dark, typically over night. DMF was evaporated under reduced pressure and the crude product was purified by reverse phase preparative chromatography (Vydac C18 column, 218TP1022; solvents A=water/0.1% TFA and B═CH$_3$CN/0.1% TFA; gradient 15-35% B over 60 min; flow 10 ml/min; detection at 254 nm), affording 5.2 mg (36%) of pure compound (analytical HPLC: Phenomenex Luna C18 column, 00G-4252-E0; solvents: A=water/0.1% TFA/B═CH$_3$CN/0.1% TFA, gradient: 20-40% B over 20 min; flow 1.0 ml/min; retention time 16.6 minutes; detection at 214 and 254 nm). Further characterisation was carried out using mass spectrometry, giving m/z value 961.9 [MH$^{2+}$].

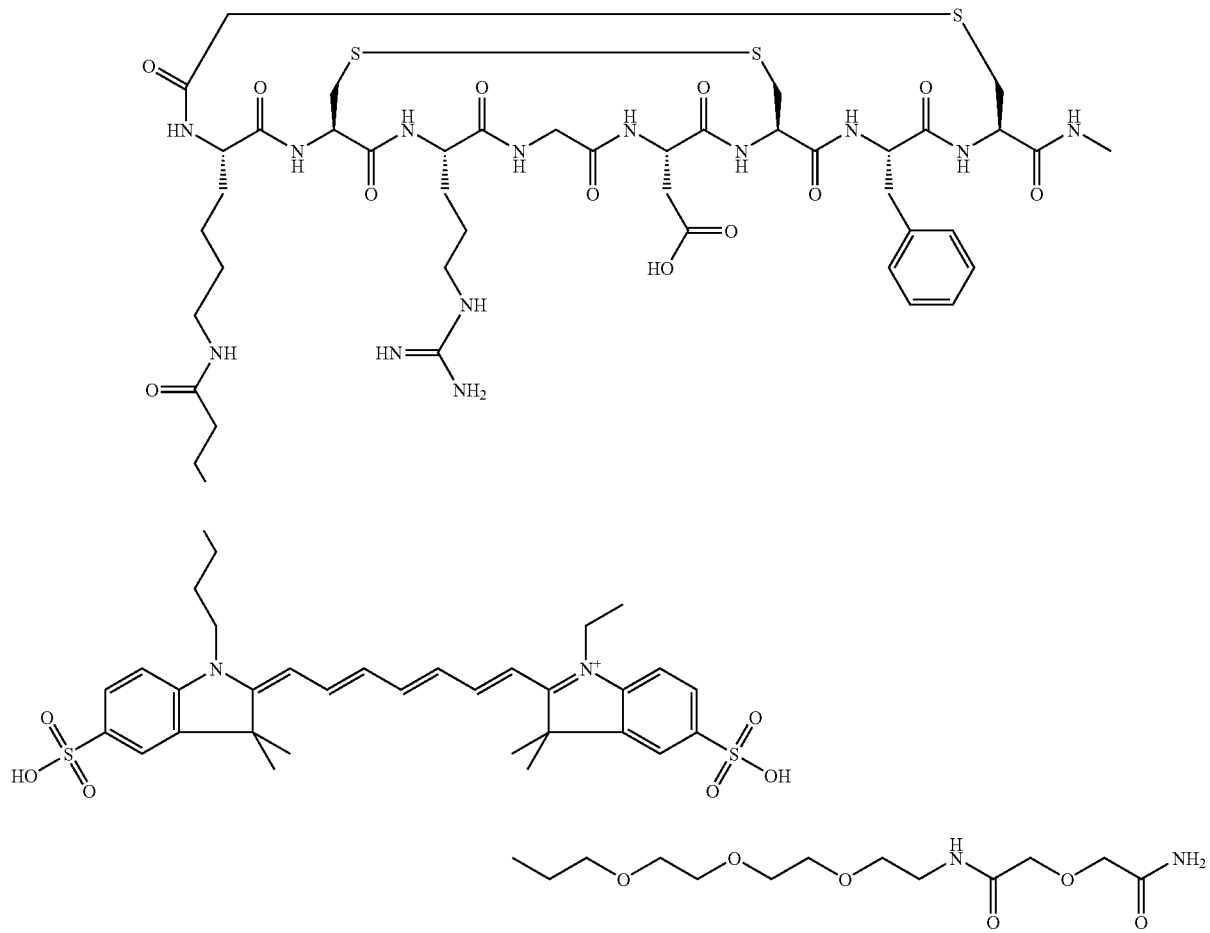

Example 4

Synthesis of Cys2-6; c[CH$_2$CO-Lys(Cy7 mono-SO$_3$)-Cys-Arg-Gly-Asp-Cys-Phe-Cys]-(PEG)n-NH$_2$ (n=1)

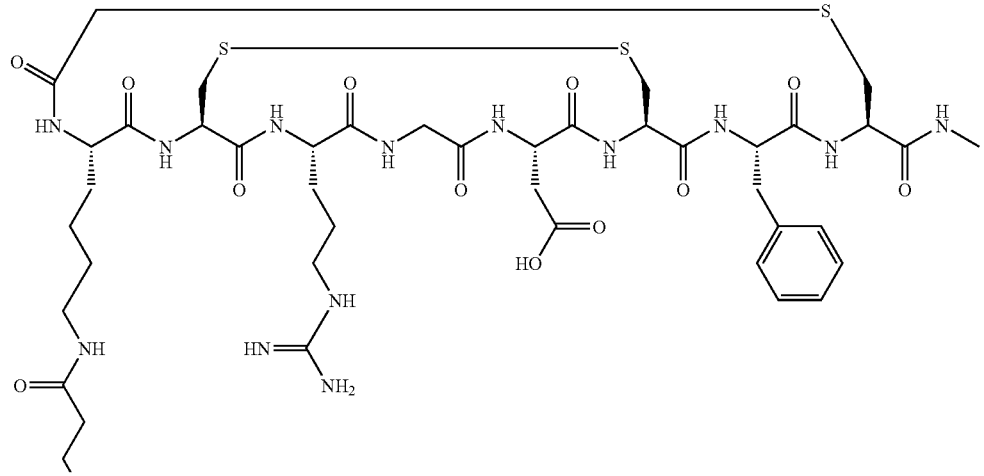

The peptide was assembled using standard solid phase synthesis methods. The chloroacetylated peptide was cleaved from the solid support and cyclized in solution by first forming the thioether bridge and then the disulphide bridge. The NHS-ester of Cy7 mono acid mono-SO$_3$ was formed by treating Cy7 (6 mg, 1 eq) with TSTU (3 mg, 0.95 eq) and NMM (5 eq) in DMF (1 ml) for 1 h. The solution was then added to the peptide (14.7 mg, 0.012 mmol, 1.2 eq) in DMF (2 ml) and the reaction was let go in the dark over night. DMF was evaporated under reduced pressure and the crude product was purified by reverse phase preparative chromatography (Vydac C18 column, 218TP1022; solvents A=water/0.1% TFA and B=CH$_3$CN/0.1% TFA; gradient 25-35% B over 60 min; flow 10 ml/min; detection at 254 nm), affording 7.0 mg (38%) of pure compound (analytical HPLC: Phenomenex Luna C18 column, 00G-4252-E0; solvents: A=water/0.1% TFA/B=CH$_3$CN/0.1% TFA, gradient: 30-40% B over 20 min; flow 1.0 ml /min; retention time 17.4 minutes; detection at 214 and 254 nm). Further characterisation was carried out using mass spectrometry, giving m/z value 922.1 [MH$^{2+}$].

Example 5

Protein Binding Analysis of Dye Conjugates Containing 1, 2 and 4 Sulphonic Acid Groups An analysis of protein binding of the dye conjugates of the invention was performed by an equilibrium dialysis and rate dialysis as described in the book "Protein-Ligand Interactions: Hydrodynamics and calorimetry", edited by Stephen E. Harding and Babur Z. Chowdhry, Oxford University Press, published 2001, chapter 2 by Bent Honoré, Department of Medical Biochemisty, University of Aarhus.

Results:

| Compound: | Protein binding (%) |
|---|---|
| No. A, from Example 1. RGD-peptide Cy5 mono-SO$_3$ | 17 |
| No. B, from Example 2. RGD-peptide Cy5 bis-SO$_3$ | 21 |
| No. C. RGD-peptide Cy5.5 4-SO$_3$ | 45 |

The example shows that cyanine dyes with a reduced number of sulphonic acid moieties when conjugated to the RGD peptide posses lower blood plasma binding and reduced non-specific binding to background tissue.

What is claimed is:

1. A compound comprising a peptidic vector and at least one cyanine dye, wherein the peptidic vector comprises the amino acid sequence $X_3$-G-D, wherein the peptidic vector and the at least one cyanine dye are coupled, and wherein
   $X_3$ represents arginine or N-methylarginine,
   G represents glycine,
   D represents aspartic acid,
   or a physiologically acceptable salt thereof.

2. A compound as claimed in claim 1 wherein the at least one cyanine dye each comprises 2, 1 or no sulphonic acid moieties.

3. A compound as claimed in claim 1 wherein the at least one cyanine dye is selected from the groups of carbacyanines, oxacyanines, thiacyanines and azacyanines.

4. A compound as claimed in claim 1 wherein the at least one cyanine dye is a carbacyanine dye.

5. A compound as claimed in claim 1 identified by the formula (VI a)

$$A-Z \qquad (VI\ a)$$

wherein A is identified by the formula (VI b)

$$R_a\text{—}C(\text{==}O)\text{-}X_1\text{—}X_2\text{—}X_3\text{-}G\text{-}D\text{-}X_4\text{—}X_5\text{—}X_6\text{—}X_7 \qquad (VI\ b)$$

and Z represents at least one cyanine dye, linked to one or more of $X_1$, $X_6$ or $X_7$ of A, the compound comprising two cyclising bridges, wherein, $X_3$, G and D defined in claim 1;

$R_a$ represents —$(CH_2)_n$— or —$(CH_2)_n$—$C_6H_4$— group, which forms part of a bridge binding to either of $X_2$, $X_4$ or $X_6$, wherein n represents a positive integer from 1 to 10, $X_1$ represents a bond or 1, 2, 3, 4 or 5 amino acid residues, wherein at least one amino acid residue is optionally functionalised with a $W_1$ group, or said amino acid residue possesses a functional side-chain chosen from an acid or amine group, $X_2$, $X_4$ and $X_6$ independently represent an amino acid residue capable of forming a disulphide or thioether cyclising bridge, $X_5$ represents a tyrosine, a phenylalanine, a 3-iodo-tyrosine or a naphthylalanine residue, and $X_7$ represents a $W_1$ group or biomodifier moiety or is absent, wherein said biomodifier moiety comprises 1 to 10 units of a monodisperse polyethylene glycol (PEG) building block;

$W_1$ is a spacer moiety chosen from glutaric, succinic acid, or a polyethylene glycol group.

6. A compound as claimed in claim 5 selected from any one of the formulas;

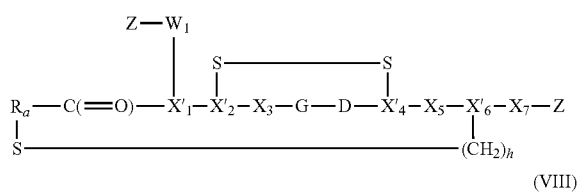

(VII)

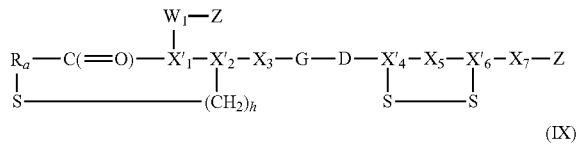

(VIII)

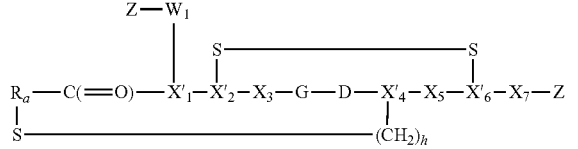

(IX)

wherein $R_a$, $X_3$, G, D, $X_5$, and $X_7$ are as defined in claim 5 and wherein $X'_1$ comprises an amino acid residue with a functional side-chain chosen from an acid or amine group, $X'_2$, $X'_4$ and $X'_6$ represent amino acid residues forming a disulphide or a thioether bond, $W_1$ is a spacer moiety as defined in claim 5 or is absent, h is a positive integer of 1 or 2, and wherein at least one of the Z groups is present, Z representing a cyanine dye.

7. A compound of formula VII as claimed in claim 6 wherein $R_a$ represents —$(CH_2)$—.

8. A compound of formula VII as claimed in claim 6 wherein $X'_1$ represents an amino acid residue with a functional side-chain chosen from an acid or amine group, the amino acid being selected from aspartic acid, glutamic acid, homolysine, lysine or diaminopropionic acid.

9. A compound of formula VII as claimed in claim 6 wherein $X'_2$, $X'_4$ and $X'_6$ independently represent a cysteine or homocysteine residue.

10. A compound of formula VII as claimed in claim 6 wherein $X_3$ represents arginine.

11. A compound of formula VII as claimed in claim 6 wherein $X_5$ represents phenylalanine, tyrosine, 3-iodo-tyrosine or naphthylalanine.

12. A compound of formula VII as claimed in claim 6 wherein $X_7$ comprises 1-10 units of a monodisperse PEG building block or is absent.

13. A compound as claimed in claim 6 wherein the cyanine dyes Z are linked to one or more of $X'_1$, $W_1$, $X_6$ or $X_7$ via an amide, sulphonamide or a thioether linkage.

14. A pharmaceutical composition comprising an effective amount of a compound as claimed in claim 1, together with one or more pharmaceutically acceptable adjuvants, excipients or diluents.

15. An optical imaging contrast agent which comprises the compound as claimed in claim 1.

16. A method of optical imaging of a human or animal body comprising administering a contrast agent as defined in claim 15 to said body, and generating an image of at least a part of said body to which said contrast agent has distributed.

17. A method of monitoring the effect of treatment of a human or animal body with a drug, said method comprising administering to said body a compound as claimed in claim 1 a composition as claimed in claim 14, and detecting the uptake of said compound or composition by cell receptors via optical imaging, said administration and detection optionally being effected before, during and after treatment with said drug.

* * * * *